United States Patent
Park

(10) Patent No.: US 10,821,052 B1
(45) Date of Patent: Nov. 3, 2020

(54) EYE MOISTURIZER

(71) Applicant: Min Gyu Park, Busan (KR)

(72) Inventor: Min Gyu Park, Busan (KR)

( * ) Notice: Subject to any disclaimer, the term of this patent is extended or adjusted under 35 U.S.C. 154(b) by 4 days.

(21) Appl. No.: 16/569,441

(22) Filed: Sep. 12, 2019

(30) Foreign Application Priority Data

Jun. 21, 2019 (KR) .......................... 10-2019-0074377

(51) Int. Cl.
*A61H 33/12* (2006.01)

(52) U.S. Cl.
CPC ..... *A61H 33/12* (2013.01); *A61H 2201/0207* (2013.01); *A61H 2201/1604* (2013.01); *A61H 2205/024* (2013.01)

(58) Field of Classification Search
CPC .............. A61H 33/12; A61H 2205/024; A61H 2201/1604; A61H 2201/0207
See application file for complete search history.

(56) References Cited

U.S. PATENT DOCUMENTS

| 2002/0124843 | A1* | 9/2002 | Skiba ..................... A61M 11/02 128/200.18 |
| 2004/0237969 | A1* | 12/2004 | Fuller ..................... A61F 9/028 128/858 |
| 2004/0256487 | A1* | 12/2004 | Collins, Jr. ......... A61M 11/005 239/338 |
| 2005/0175330 | A1* | 8/2005 | Kaizuka ................. A61H 33/12 392/405 |
| 2005/0240162 | A1* | 10/2005 | Chen ..................... A61F 9/0026 604/298 |
| 2008/0200848 | A1* | 8/2008 | Avni ..................... A61M 11/00 601/46 |
| 2013/0160760 | A1* | 6/2013 | Chen ..................... A61H 33/12 128/200.19 |
| 2018/0200106 | A1* | 7/2018 | Zoumalan ............. A61F 7/0085 |
| 2018/0318166 | A1* | 11/2018 | Oda ......................... A61F 7/03 |

FOREIGN PATENT DOCUMENTS

| KR | 2004212240000 | | 7/2006 |
| KR | 2004302990000 | | 10/2006 |
| KR | 20190066730 A | * | 6/2019 |
| WO | WO-2017156050 A1 | * | 9/2017 | ............ A61M 11/02 |

\* cited by examiner

*Primary Examiner* — Gary Jackson
*Assistant Examiner* — Sebastian X Lukjan
(74) *Attorney, Agent, or Firm* — IPLA P.A.; James E. Bame

(57) ABSTRACT

An eye moisturizer includes: a pair of hot water containers for storing hot water from which water vapor is generated; a connection panel coupled to the hot water containers to allow the hot water containers to be spaced apart from each other; a glabella support disposed between the hot water containers to maintain a height of a user's face; a lower support protruding from the underside of the connection panel to prevent falling; and water vapor discharge portions formed on tops of the hot water containers or the connection panel to discharge the water vapor therefrom, while preventing the hot water containers from coming into contact with the eyes, where the waver vapor is fed to the eyes seeing vertically the hot water containers and to the skin around the eyes.

2 Claims, 6 Drawing Sheets

EYE MOISTURIZER

CROSS REFERENCE

The present application claims the benefit of Korean Patent Application No. 10-2019-0074377 filed Jun. 21, 2019 with the Korean Intellectual Property Office, the entire contents of which are incorporated herein by reference.

BACKGROUND

The present invention relates to an eye moisturizer, and more particularly, to an eye moisturizer that is capable of efficiently feeding water to dry eyes and skin around the eyes, while enabling eye movements.

BACKGROUND ART

If a tear film of an eye becomes too dried, it does not perform lubrication well on the surface of the eye, so that even the surface of the eye becomes dried to make the eye feel unpleasant and easily fatigued and become blurry in the view field thereof. Such dry eye syndrome gives many uncomfortable feelings to the eyes during reading a book, computing, wearing contact lenses, and around an air conditioner or heater. If the eyes are dried, the skin around the eyes is naturally dried to undesirably cause skin aging. Accordingly, there is a need to develop a new technology capable of directly feeding water to the eyes to prevent the eyes from being dried.

As one example of conventional technologies for solving the above-mentioned problems, Korean Utility Model Registration No. 0430299 (Issued on Nov. 13, 2006) suggests a warming pack only for eyes that includes: a heating part (10) having a piezo-electric material (13) adapted to convert mechanical energy into electrical energy, a heating material (12) changed from solid into liquid if the piezo-electric material (13) operates and adapted to generate thermal energy when reduced from the liquid to the solid, and a vinyl pack (11) for accommodating the heating material (12); and a massage sheet (20) having massage water contained therein in such a manner as to be warm by means of the thermal energy generated from the heating part (10) to generate water steam.

As the conventional warming pack comes into close contact with the eyes, however, chemicals may leak from the heating part having the heating material made of any one of sodium thiosulfate and sodium acetate, thereby giving bad influences to the eyes. Further, the conventional warming pack is a disposable product so that if the massage water contained in the massage sheet is dried, the warming pack cannot be used anymore, thereby making it impossible to be used again to undesirably cause environmental pollution.

As another example of the conventional technologies, further, Korean Utility Model Registration No. 0421224 (Issued on Jul. 10, 2006) suggests a mugwort fumigator only for eyes that is worn on a user's face to supply the fumigation generated therefrom to the eyes so that good incredients contained in mugwort are fed to the eyes and the acupuncture points around the eyes, thereby improving blood circulation and reducing eye fatigue. The mugwort fumigator only for eyes includes a fumigation generator (52) adapted to receive power to generate fumigation and having a mugwort pad (51) accommodated therein and a fumigation supplier (53) adapted to supply the fumigation generated from the fumigation generator (52) to the eyes.

According to the above-mentioned conventional technology, however, there is a need to perform a relatively complicate coupling process wherein the fumigation supplier (53) is separated from the fumigation generator (52), the mugwort pad (51) to which water is sprayed is seated on a fumigation base (60), and next, the fumigation supplier (53) and the fumigation generator (52) are coupled again to each other, and further, the power inconveniently has to be supplied from the outside to the fumigation generator (52) so as to generate the fumigation. As eye pads (70) come into contact with the eyes, furthermore, they fail to naturally supply heat to the eyes and the skin around the eyes, so that a boundary around the eyes may be unnaturally formed. Also, discharge holes (74) are too small and the mugwort fumigator only for eyes has a shape of a band to undesirably cause the wearer's head to be compressed when worn. Accordingly, if hot fumigation is suddenly generated, the wearer may be burnt, and as the whole weight of the mugwort fumigator is increased due to the composite structure thereof, the wearer's head, neck and shoulders may become fatigued.

Further, the mugwort fumigator is not easy to be disassembled and cleaned due to the complication in the whole structure, and accordingly, it is hard to keep safe sanitation for the mugwort fumigator.

Accordingly, there is a need to develop a new technology capable of preventing eyes and skin around the eyes from being dried, while solving the above-mentioned problems in the conventional technologies.

SUMMARY OF THE INVENTION

Accordingly, the present invention has been made in view of the above-mentioned problems occurring in the related art, and it is an object of the present invention to provide an eye moisturizer that is configured to easily feed water vapor to eyes and the skin around the eyes, to improve blood circulation through the heat contained in the water vapor to prevent skin aging, and to enable eye movements through focus inducers.

To accomplish the above-mentioned object, according to the present invention, there is provided an eye moisturizer including: a pair of hot water containers for storing hot water from which water vapor is generated and fed to eyes and skin around the eyes seen vertically therefrom; a connection panel coupled to the hot water containers to allow the hot water containers to be spaced apart from each other; a glabella support disposed between the hot water containers to maintain up and down distances between the hot water containers and the eyes; and water vapor discharge portions formed on tops of the hot water containers or the connection panel to discharge the water vapor therefrom, while preventing the hot water containers from coming into contact with the eyes.

According to the present invention, desirably, the eye moisturizer further includes focus inducers formed on the bottom surfaces of the hot water containers to induce movements of the pupils so that eye movements are performed.

According to the present invention, desirably, the eye moisturizer further includes distance adjusting means formed on the hot water containers and the connection panel to allow the hot water containers and the connection panel to be slidingly detached from each other and to allow a distance between the hot water containers to be adjusted.

As mentioned above, the eye moisturizer according to the present invention is configured to feed water to the eyes and the skin around the eyes to avoid dry eye syndrome, so that if the eye moisturizer is constantly used before the eyes are dried, the dry eye syndrome can be protected.

In addition, the eye moisturizer according to the present invention is configured to allow the eyes and skin to become warm and to thus make a blood stream around the eyes gently flow, so that blood circulation becomes good to prevent the skin around the eyes from being aged, thereby improving skin wrinkles.

Further, the eye moisturizer according to the present invention is configured to additionally perform the eye movements through the focus inducers so that the ocular muscles can be strengthened, while feeding the water to the eyes is being enhanced, and the eye moisturizer according to the present invention is simple in configuration so that it can be lightweight and easy to be carried.

Furthermore, the eye moisturizer according to the present invention is configured to have the water vapor discharge means for preventing the eyes and the skin around the eyes from being burnt due to excessive water vapor.

Also, the eye moisturizer according to the present invention has an open configuration so that the manufacturing cost thereof is reduced, the manufacturing process is easy to enable mass production and high productivity, and the washing is easy to enable the eye moisturizer to be sanitarily controlled.

DETAILED DESCRIPTION OF THE INVENTION

Hereinafter, the present invention will be in detail explained with reference to the attached drawings.

Figure 1:
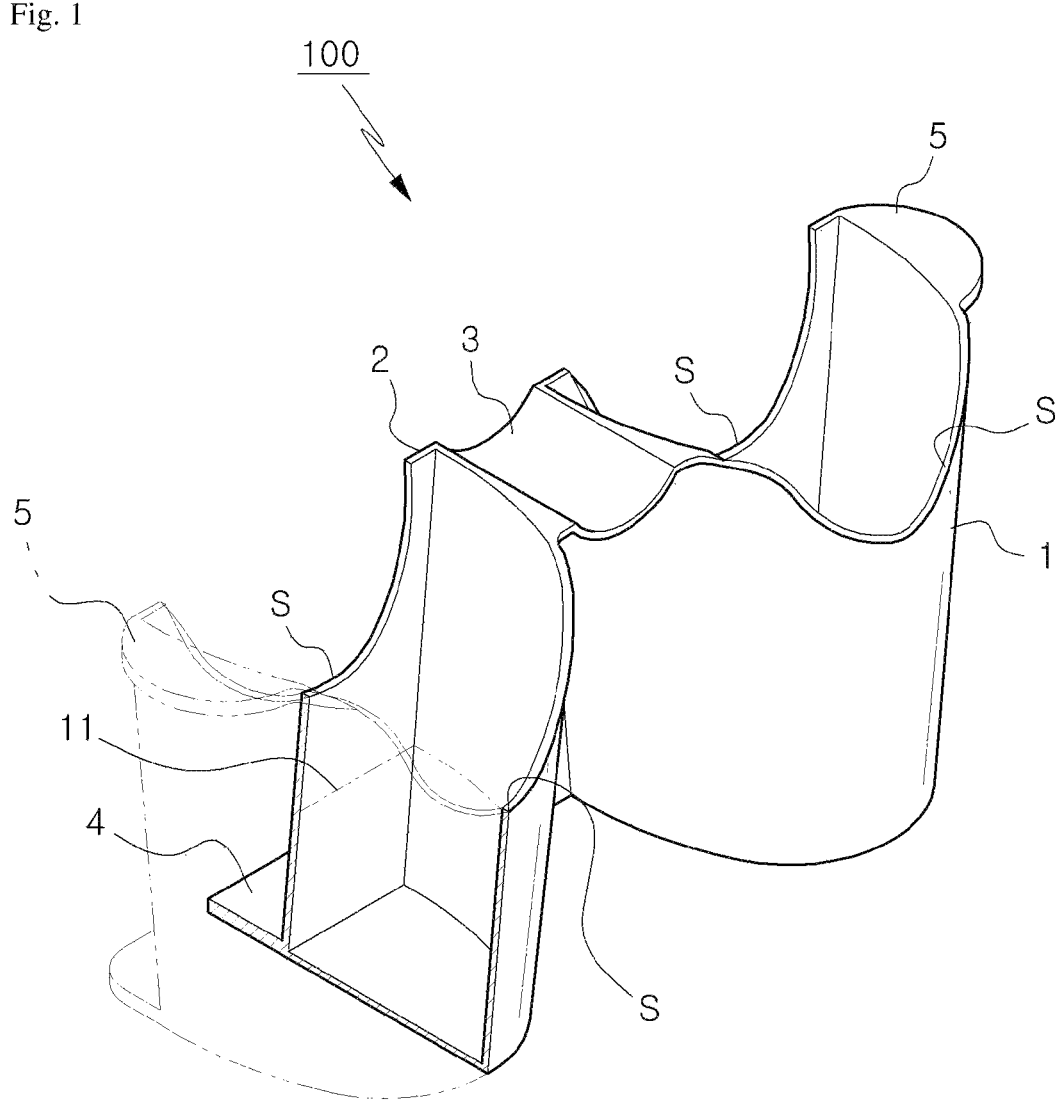
FIG. 1 is a front perspective view showing an eye moisturizer according to one embodiment of the present invention.
Figure 2:
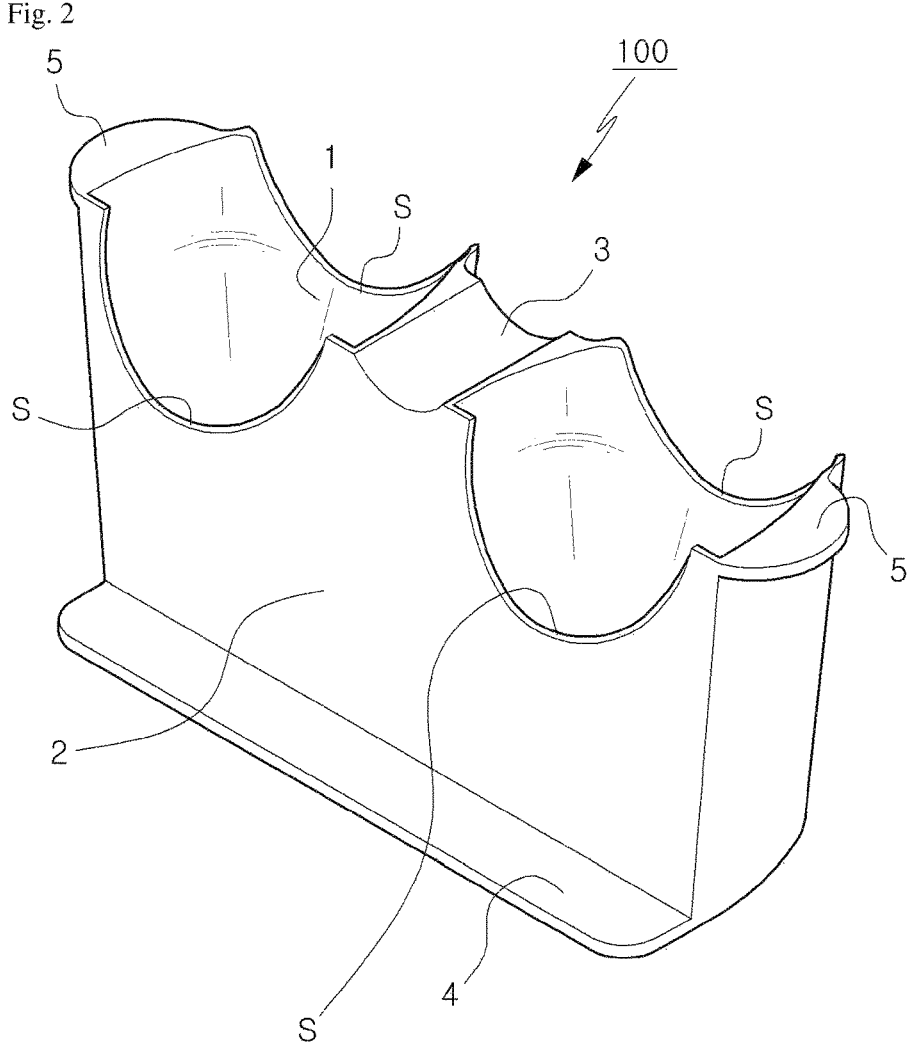
FIG. 2 is a rear perspective view showing the eye moisturizer according to one embodiment of the present invention.
Figure 3:
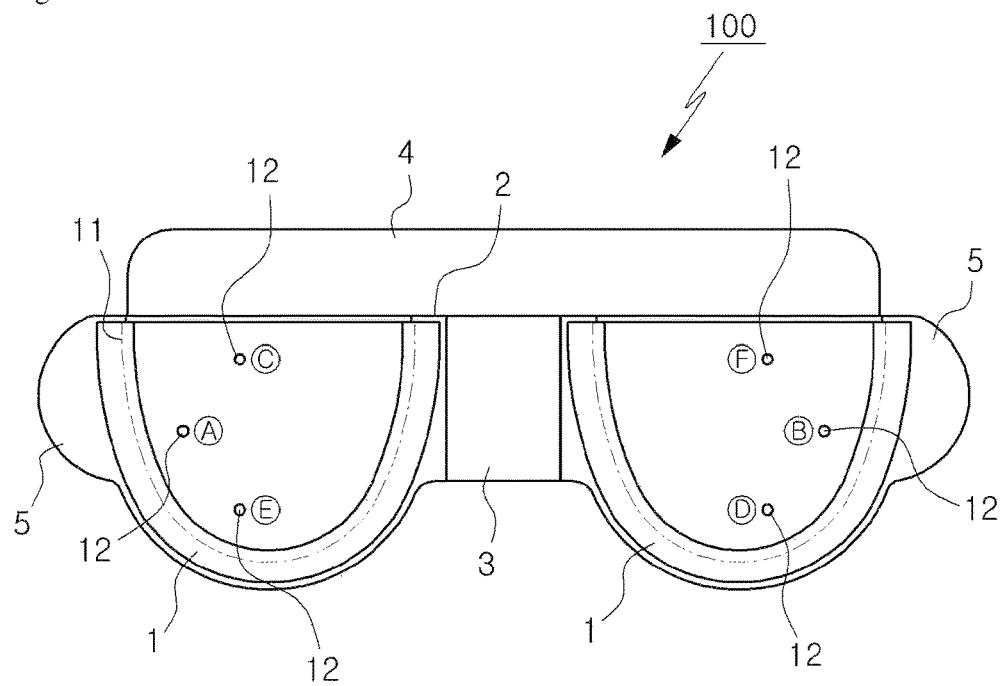
FIG. 3 is a plan view showing the eye moisturizer according to one embodiment of the present invention.

As shown in FIGS. 1 to 3, an eye moisturizer 100 according to one embodiment of the present invention is configured to have a pair of hot water containers 1 spaced apart from each other in such a manner as to be located at vertical positions to the human eyes.

Further, the eye moisturizer 100 has a connection panel 2 disposed on one side of the pair of hot water containers 1 so that the pair of hot water containers 1 is connected to each other.

Furthermore, the eye moisturizer 100 has a glabella support 3 disposed between the top end peripheries of the hot water containers 1 to support the glabella and nose at the time when the eye moisturizer 100 is used.

Also, the eye moisturizer 100 has a bottom support 4 protruding from the bottom periphery of the connection panel 2 in the opposite direction to the surface of the connection panel 2 coupled to the hot water containers 1.

In addition, water level indicators 11 are located on the inner surfaces of the hot water containers 1 to indicate a reference for an appropriate amount of hot water, and focus inducers 12 are formed on the inner bottom surfaces of the hot water containers to induce focuses of eyes while the eye moisturizer 100 is being used, so that the eye movements can be performed.

Further, handles 5 protrude outward from the top end of the connection panel 2 or the top end peripheries of the hot water containers 1, so that there is no need to hold the hot water containers by a user's hands, thereby in advance preventing occurrence of bacterial contamination.

The above-mentioned components are made of a synthetic resin, and also, they are formed unitarily with one another.

Figure 4:
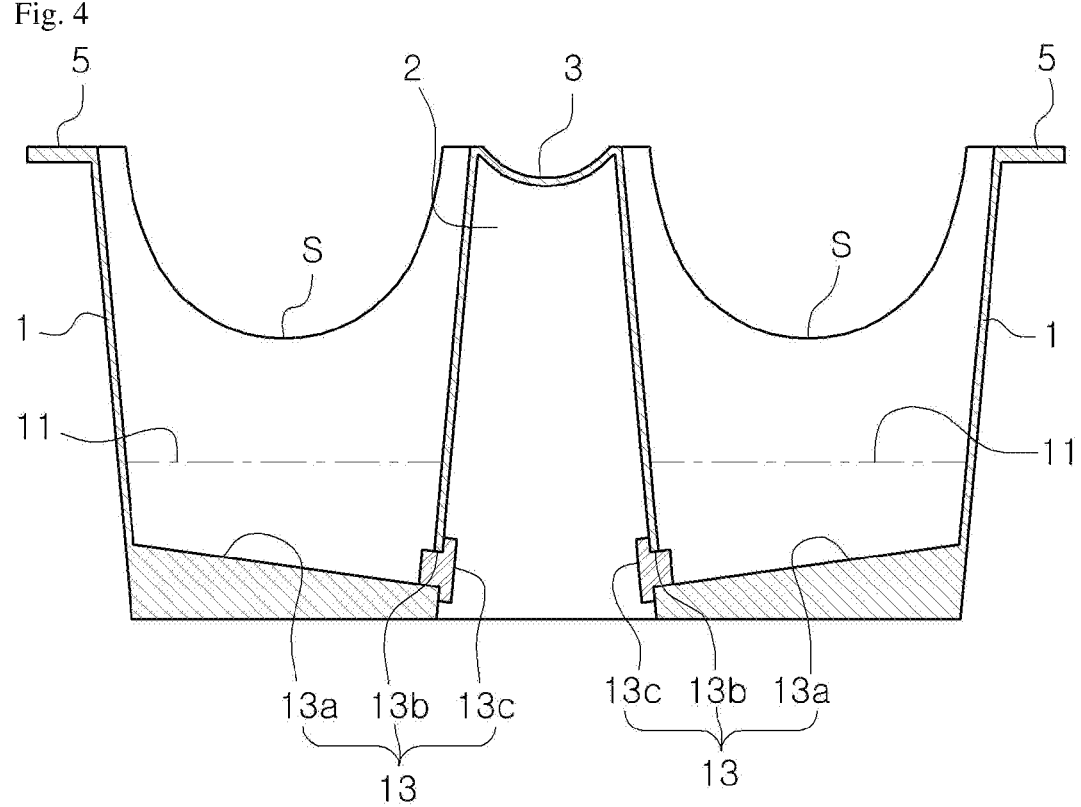
FIG. 4 is a front sectional view showing an eye moisturizer according to another embodiment of the present invention.

According to another embodiment of the present invention, as shown in FIG. 4, the eye moisturizer 100 further includes discharging means 13 disposed on the lower portions of the hot water containers 1.

Each discharging means 13 includes a slant surface 13a formed on the bottom surface of the corresponding hot water container 1 to induce the water in the hot water container 1 in one direction, a discharge hole 13b formed on one side of the hot water container 1 to discharge the induced water, and a fitting type stopper 13c for sealing the discharge hole 13b if it is desired to store the water in the hot water container 1.

Figure 5:
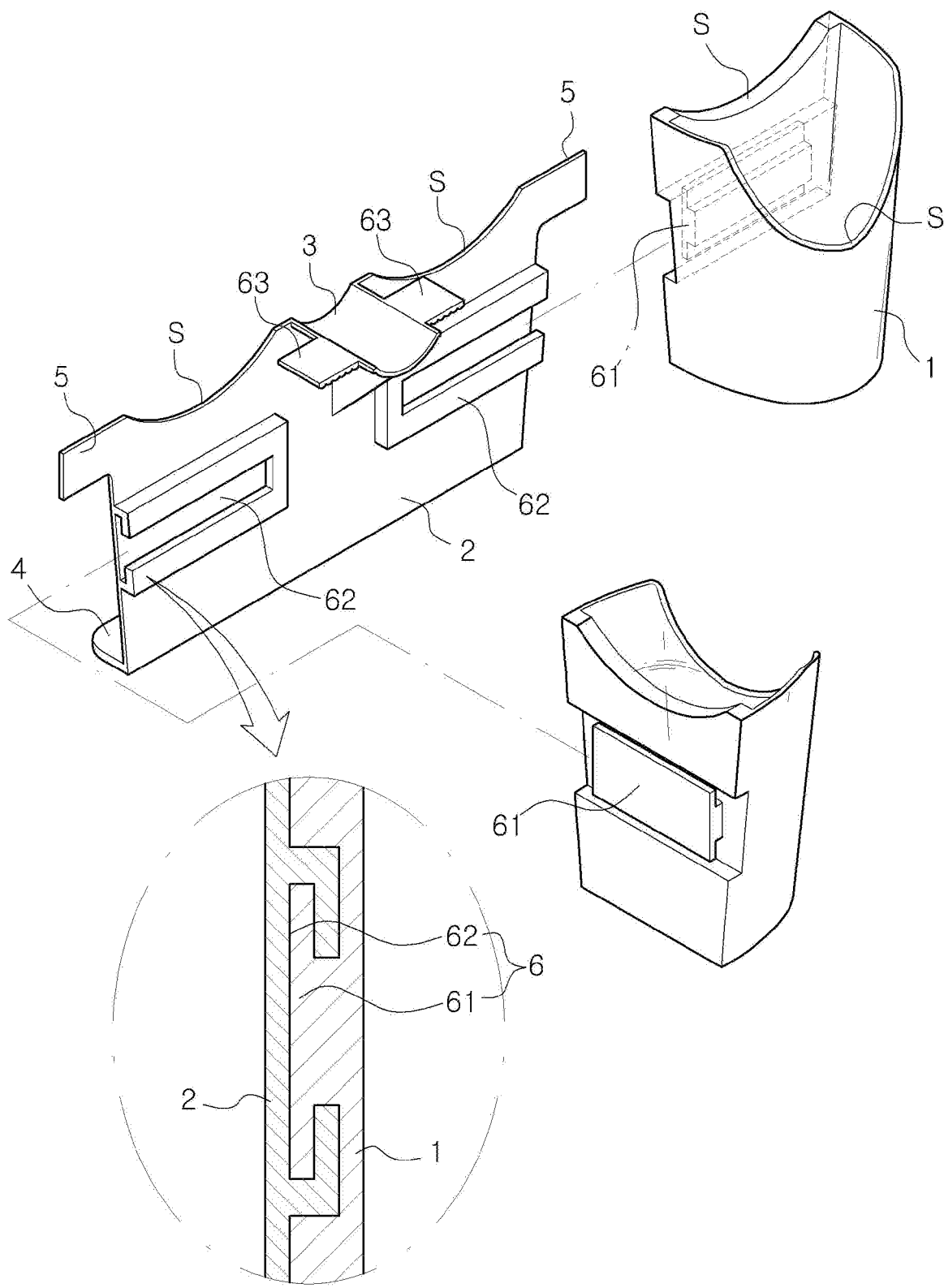
FIG. 5 is an exploded perspective view showing an eye moisturizer according to yet another embodiment of the present invention.

According to yet another embodiment of the present invention, as shown in FIG. 5, the eye moisturizer is configured to allow the hot water containers 1 to slide to left and right sides, so that they can be detachable from the connection panel 2, and also, they can be adjusted in distance.

In detail, a pair of distance adjusting means 6 slides correspondingly along the hot water containers 1 and the connection panel 2 to allow the hot water containers 1 to be detached from the connection panel 2 or to be adjusted in distance, so that the hot water containers 1 can be individually separated from each other.

For example, each distance adjusting means 6 includes a coupling protrusion 61 formed in a longitudinal direction on one of the hot water container 1 and the connection panel 2 and a coupling groove 62 formed on the other of the hot water container 1 and the connection panel 2 in such a manner as to be fastened correspondingly to the coupling protrusion 61.

A glabella support 3 protrudes from the center of the top end of the connection panel 2, handles 5 protrude from the sides of the connection panel 2, and a bottom support 4 protrudes from the bottom end of the connection panel 1.

The glabella support 3 has locking pieces 63 protruding from both sides thereof, and the locking pieces 63 have protrusions formed on the undersides thereof in such a manner as to be locked on top end peripheries of the hot water containers 1, so that the hot water containers 1 can be fixed in position and the glabella support 3 can be prevented from sagging and breakage.

Further, a vertical reinforcing rib may be disposed on the underside of the glabella support 3.

Now, an explanation on the operation of the eye moisturizer 100 according to the present invention will be given.

Figure 6:
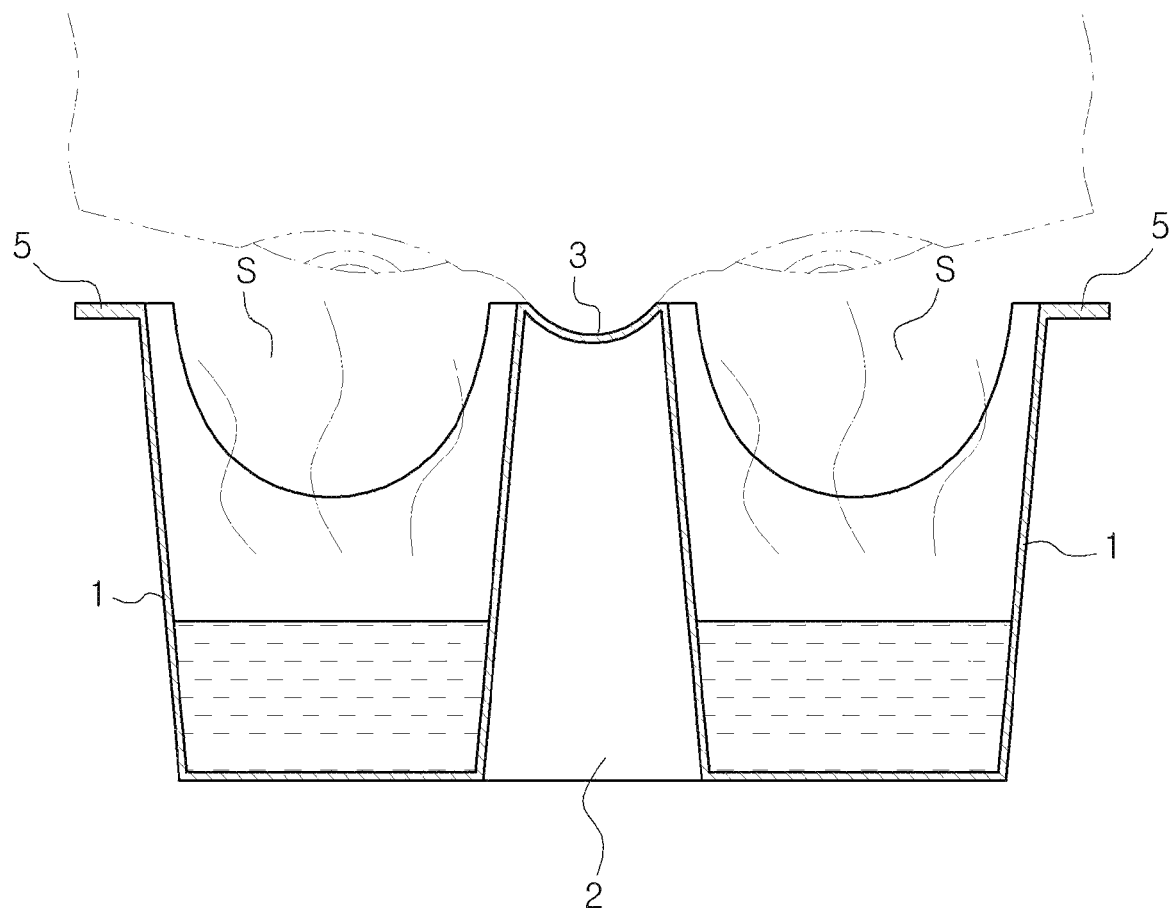
FIG. 6 is a front sectional view showing an operation of the eye moisturizer according to the present invention.

As shown in FIG. 6, the eye moisturizer 100 is placed on a given position having no shaking, like a desk, and next, hot water is poured into the hot water containers 1 up to the heights indicated by the water level indicators 11, thereby finishing the preparation for the use of the eye moisturizer 100.

The hot water has an appropriate temperature at which it can be evaporated at a room temperature to generate water vapor causing no burn.

The user bends his or her neck or waist to allow his or her eyes to vertically see the hot water containers 1, and the heights of the user's eyes are close to the hot water containers 1 to a degree where tops of his or her glabella or nose come into contact with the glabella support 3.

A portion of the water vapor coming into contact with the eyes and the skin is condensed and moisturizedly attached to the surfaces of the dry eyes and skin.

Accordingly, the water is absorbed to the surfaces of the eyes and skin, thereby naturally enabling water feeding to them, and as the water vapor is warmer than the room temperature, further, pores of the skin are open to make the water more easily absorbed to the skin.

Figure 7:
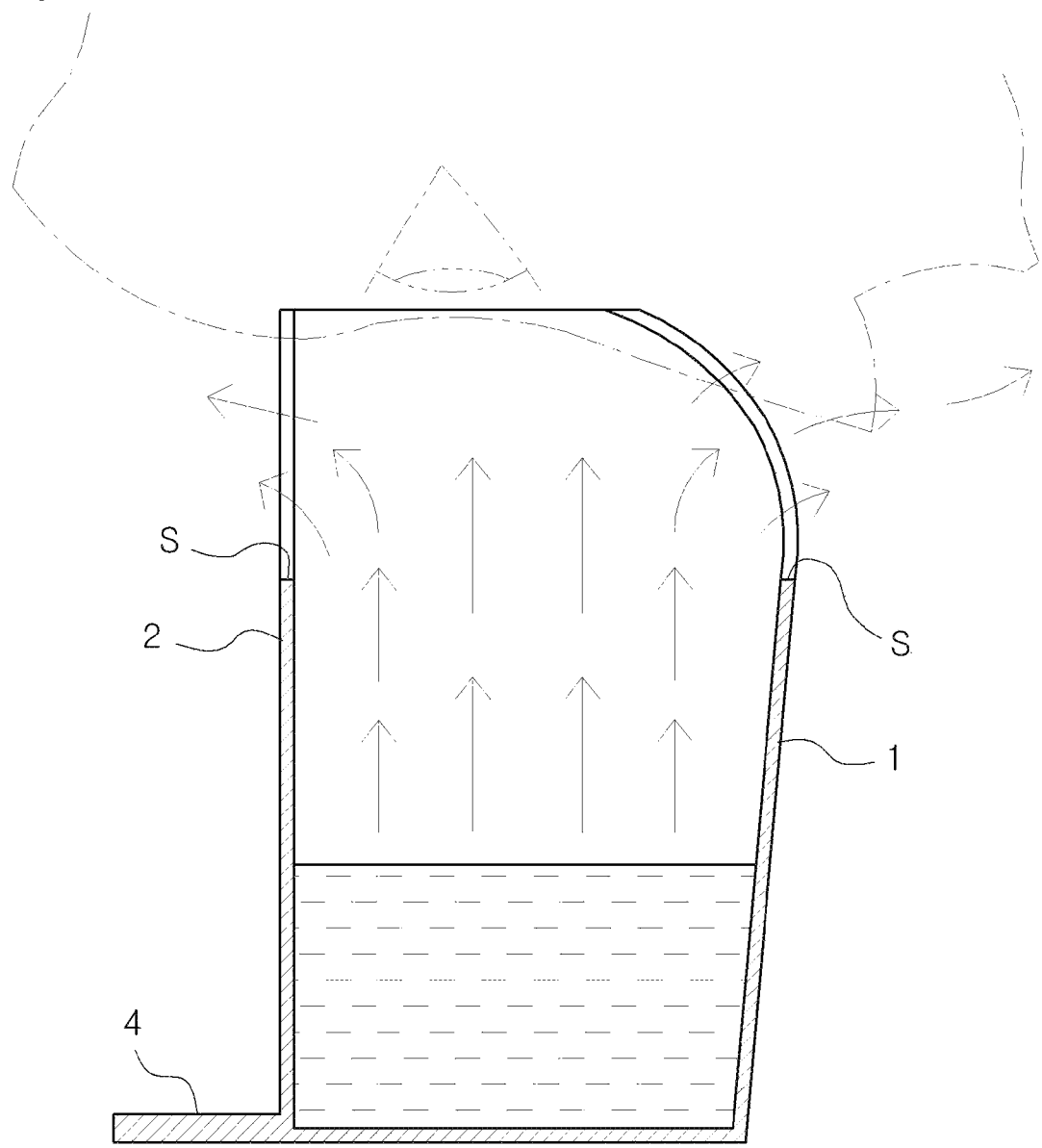
FIG. 7 is a side sectional view showing the operation of the eye moisturizer according to the present invention.

The water vapor continuously rises from the hot water, and accordingly, the rest of water vapor not condensed on the eyes and skin has to be appropriately discharged to prevent the temperatures of the eyes and skin from being excessively raised and also to prevent the eyes and skin from being burnt. To do this, as shown in FIG. 7, water vapor discharge portions S are spaced apart from the eyes and skin to discharge the rest of water vapor to the outside.

If the eyes stop, without any movements, during exposed to the water vapor, the water is fed just to only small portions of the spherical eyes. So as to allow the portion to which the water is fed to be enlarged and also to allow ocular muscles to be strengthened, accordingly, the pupils see the focus inducers 12 as shown in FIG. 3 in a predetermined sequential order, so that the eyes are turned to allow areas to which the water is fed to be naturally enlarged.

For example, if the pupils see the plurality of focus inducers 12 in the order of alphabets A to F as shown in FIG. 3, while moving repeatedly with appropriate times, the eye movements can be naturally performed and the water can be fed to every area of the eyes.

According to another operation of the eye moisturizer 100, if it is desired to discharge the hot water in the hot water containers 1 or discharge the water cold at the room temperature from the hot water containers 1, the eye moisturizer 100 is turned over to discharge the water to a sink or basin, but in this case, the glabella support 3 gets in touch with water and becomes thus wet to make the user feel unpleasant, so that the water has to be inconveniently removed from the glabella support 3.

At this time, if the discharging means 13 as shown in FIG. 4 are disposed on the lower portions of the hot water containers 1, a cup is located on the undersides of the hot water containers 1 to receive the water discharged from the hot water containers 1 through the discharging means 13.

If the discharge holes 13b are open by removal of the stoppers 13c, the water in the hot water containers 1 flowing along the slant surfaces 13a is discharged through the discharge holes 13b, and if the discharging is finished, the stoppers 13c are coupled sealingly to the discharge holes 13b again.

If the eye moisturizer 100 is configured to allow the hot water containers 1 to detachably slide along the connection panel 2, as shown in FIG. 5, the hot water containers 1 can be washed and kept individually, and also, only the containers contaminated due to the use for a long period of time can be exchanged with new ones.

The hot water containers 1 and the connection panel 2 are detachably mounted on each other by means of the distance adjusting means 6, and the distance between the hot water containers 1 can be adjusted according to a degree sliding to the left and right sides.

If the distance between the hot water containers 1 is adjusted, the eye moisturizer 100 can be used for every person who has small or wide glabella, irrespective of his or her sex and age.

So as to enhance the support force of the glabella support 3 coupled to the top end of the connection panel 2, the reinforcing rib is disposed on the underside of the glabella support 3, and otherwise, the locking pieces 63 protrude from both sides of the glabella support 3 in such a manner as to be locked onto the top end peripheries of the hot water containers 1.

Also, the multi-stepped locking protrusions are formed on the undersides of the locking pieces 63 to allow the top end peripheries of the hot water containers 1 to be fixedly locked thereonto at the time when the hot water containers 1 slide.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An eye moisturizer comprising:
    a pair of hot water containers for storing hot water from which water vapor is generated and fed to eyes and skin around the eyes seen vertically therefrom;
    a connection panel coupled to the hot water containers to allow the hot water containers to be spaced apart from each other;
    a glabella support disposed between the hot water containers to maintain up and down distances between the hot water containers and the eyes; and
    water vapor discharge portions formed on tops of the hot water containers or the connection panel to discharge the water vapor therefrom, while preventing the hot water containers from coming into contact with the eyes; and
    focus inducers formed on bottom surfaces of the hot water containers to induce pupil movements so that eye movements are performed.

2. The eye moisturizer according to claim 1, further comprising distance adjusting means formed on the hot water containers and the connection panel to allow the hot water containers and the connection panel to be slidingly detached from each other and to allow a distance between the hot water containers to be adjusted.

* * * * *